United States Patent [19]

Broecker et al.

[11] Patent Number: 4,623,668

[45] Date of Patent: Nov. 18, 1986

[54] PREPARATION OF METHANOL

[75] Inventors: Franz J. Broecker, Ludwigshafen; Gerd Duembgen, Dannstadt-Schauernheim; Wolfgang Pies, Frankenthal; Gottfried Schlichthaerle, Neustadt; Guenter Weber, Linden, all of Fed. Rep. of Germany

[73] Assignee: BASF Aktiengesellschaft, Fed. Rep. of Germany

[21] Appl. No.: 614,142

[22] Filed: May 25, 1984

[30] Foreign Application Priority Data

May 25, 1983 [DE] Fed. Rep. of Germany ......... 331855

[51] Int. Cl.$^4$ ...................... C07C 27/06; C07C 31/04
[52] U.S. Cl. .................................... 518/709; 518/713; 502/38
[58] Field of Search ................................ 518/713, 709

[56] References Cited

U.S. PATENT DOCUMENTS

| 4,375,424 | 3/1983 | Slaugh | 518/713 |
| 4,423,155 | 12/1983 | Bell et al. | 518/713 X |
| 4,440,668 | 4/1984 | Chang et al. | 518/713 |
| 4,507,403 | 3/1985 | Asakawa | 518/713 |

OTHER PUBLICATIONS

Herman et al., J of Catalysis 56, 407–429, 1979.

*Primary Examiner*—Howard T. Mars
*Attorney, Agent, or Firm*—Keil & Weinkauf

[57] ABSTRACT

Methanol is prepared by catalytic conversion of a synthesis gas mixture, containing hydrogen, carbon monoxide, carbon dioxide and/or water, at from 200° to 320° C. and under from 30 to 300 bar in adiabatic and/or isothermal reactions in the presence of a catalyst containing copper and zinc, by a process in which the fresh catalyst is reduced with a hydrogen-containing gas before the start-up of the process, and then the synthesis is started under conventional conditions and is continued until the formation of methanol in the reaction zone has declined substantially, after which the reaction is interrupted and the catalyst is regenerated.

1 Claim, No Drawings

PREPARATION OF METHANOL

The present invention relates to a process for the preparation of methanol by reacting hydrogen, carbon monoxide, carbon dioxide and/or steam in the presence of a catalyst containing copper and zinc.

At present two principal methods for the preparation of methanol from synthesis gases which contain, inter alia, hydrogen, carbon monoxide, carbon dioxide and water, are known. The earlier procedure, also known as the high pressure methanol synthesis, uses catalysts based on zinc oxide and chromium oxide. These catalysts are insensitive to a number of poisons, eg. sulfur and chlorine, and are very resistant to aging. However, the Cr/Zn catalysts are not very reactive; they require high reaction temperatures, eg. 320°–380° C., and the equilibrium position makes high reaction pressures, eg. 300–340 bar, necessary.

The more recent method, also known as the low pressure methanol synthesis, uses catalysts containing copper and zinc. These catalysts are substantially more active and permit lower reaction temperatures, eg. 220°–270° C., and the more favorable equilibrium position at low temperatures results in a technically simpler procedure, since this synthesis can be carried out under relatively low pressures, eg. 50–100 bar.

The catalysts containing copper and zinc have the disadvantage of a higher tendency to become deactivated. There are a large number of causes of catalyst aging, and the individual deactivation mechanisms are still substantially unexplained. Aging may be due to, for example, a reduction in the number of active catalytic centers as a result of temperature-related recrystallization, or blocking of the active centers, for example because of reaction with sulfur-containing or chlorine-containing catalyst poisons. Furthermore, the active catalytic surfaces may become coated with other substances, for example with decomposition products of metal carbonyls or with compounds produced in competing reactions. Attempts have also been made to use oxygen-containing gases to reactivate Cu-containing and Zn-containing bifunctional catalysts which are used for the dimethyl ether synthesis and also contain chromium and/or large amounts of acidic and dehydrating components. The formation of carbon black or coke-like deposits, which is observed in the dimethyl ether synthesis carried out at above 300° C. in the presence of dehydration catalysts and which may be regarded as one of the main causes of deactivation in this synthesis, is generally believed to be without significance for the low pressure methanol synthesis carried out at low temperatures (Ullmann, 4th Edition, Vol. 16, page 627).

Attempts have also been made to increase the life of copper-containing and zinc-containing low pressure methanol catalysts by pre-purifying the synthesis gas used. Adding promoters to increase the thermal stability of the catalysts has also often been proposed.

Nevertheless, the low pressure methanol catalysts undergo considerable aging, which cannot be prevented by any of the conventional measures and makes it necessary to replace the catalyst after a certain time-on-stream. This procedure is expensive because fresh catalyst has to be provided, and is also technically complicated and time-consuming because of the measures involved in removing the aged catalyst and introducing the fresh one.

It is an object of the present invention to provide a process which makes it possible completely or partially to eliminate the consequences of aging, which is partly or completely specific to the methanol synthesis, and to restore the initial activity of the Cu/Zn catalyst completely or to a substantial extent.

It is a particular object of the present invention to match up the procedure for introducing the catalyst and reducing it to the operating state, the monitoring of the course of the reaction to maintain the optimum duration, and the regeneration.

We have found that this object is achieved, and that the process for the preparation of methanol by catalytic conversion of a synthesis gas mixture, containing hydrogen, carbon monoxide, carbon dioxide and/or water, at from 200° to 320° C. and under from 30 to 300 bar in adiabatic and/or isothermal reactions in the presence of a catalyst containing copper and zinc can be optimized in the desired manner, if the fresh catalyst is first reduced with a hydrogen-containing gas before the start-up of the process, under atmospheric or slightly superatmospheric pressure at temperatures increasing from 150° to 250° C., the reduction being continued until the formation of water from the reduction reaction substantially declines, and then the synthesis is started under conventional conditions and is continued until the formation of methanol in the reaction zone has declined substantially, after which the reaction is interrupted and the catalyst is regenerated.

In a particular embodiment, the catalyst is flushed with an inert gas, eg. nitrogen or methane, at from 10° to 300° C. immediately after the reaction has been interrupted, and is then regenerated in situ. If the catalyst is flushed with methane, it is advisable to change over to flushing with nitrogen before carrying out the regeneration, in order to remove final residues of methane from the catalyst zone before the oxygen required for the regeneration is passed in.

The regeneration is advantageously carried out under atmospheric or moderately superatmospheric pressure, by passing an oxygen-containing gas over the catalyst at from 150° to 200° C., the oxygen content being adapted to the particular temperature during the entire course of the regeneration, and the passage of the oxygen-containing gas being continued until the peak of the temperature profile has moved across the entire catalyst.

In carrying out the process, it is advantageous, before the start-up of the process, to reduce the fresh catalyst under atmospheric or slightly superatmospheric pressure at temperatures increasing from 150° to 250° C., by passing a hydrogen-containing gas, eg. a nitrogen/hydrogen or a nitrogen/synthesis gas mixture, over the catalyst. Advantageously, the temperature is increased from 150° to 180° C. at the start-up, and is only slowly increased further, for example to 230° C., when the formation of water of reaction has declined, ie. when the principal reaction is complete.

The synthesis can then be started under conventional conditions.

The low pressure methanol synthesis is carried out under from 30 to 300, preferably from 40 to 120, bar and at from 200° to 320° C., preferably from 230° to 280° C., under virtually isothermal and/or adiabatic conditions. The catalysts used contain from 8 to 70% by weight of CuO and preferably from 15 to 60% by weight of ZnO, and can additionally contain metal compounds of Main Groups II and III of the Periodic Table, eg. magnesium and aluminum, and/or of Subgroups III to VII, eg.

lanthanum, thorium, vanadium, chromium and manganese, in amounts of from 0 to 50% by weight of metal oxide. Preferably used catalysts additionally contain from 0 to 40, advantageously from 1 to 8, % by weight of $Al_2O_3$ and/or from 0 to 35, advantageously from 1 to 15, % by weight of $Cr_2O_3$ and/or from 0 to 15, advantageously from 2 to 10, % by weight of $V_2O_5$. The catalysts can be prepared by precipitation from aqueous solutions of appropriate metal salts, or by impregnation of a carrier which is essentially catalytically inert, followed by drying and calcination. In order to avoid the formation of dimethyl ether, the catalysts advantageously do not contain any dehydrating components, eg. zeolites and/or $\gamma$-$Al_2O_3$. An example of a suitable catalyst is the Cu/Zn/Al catalyst described in Example 1, from German Pat. No. 2,846,614.

The advantage of the novel process is that substantial reactivation is achieved without replacing the catalyst, ie. removing catalyst from the reactor and introducing fresh catalyst; depending on the procedure, regeneration can be carried out once or repeatedly, and the overall life of the catalyst is thus substantially prolonged. Even when regeneration is repeated, the process is carried out in the manner described.

The Examples which follow illustrate the process according to the invention.

EXAMPLE 1

A low pressure methanol catalyst containing 36% by weight of CuO, 48% by weight of ZnO and 3% by weight of $Al_2O_3$ is mixed with 2% by weight of graphite and pressed to give 5×5 mm pills. This catalyst is introduced into a tube reactor operated under quasi-isothermal conditions, and is activated by reduction at 180° C. under atmospheric pressure, in a single continuous procedure, with 300–400 l (S.T.P.) per kg per hour of a hydrogen/nitrogen mixture (1 vol. % of $H_2$). The course of the activation is monitored via the formation of water in the reduction reaction. When water is no longer present in the mixture emerging from the reactor, the temperature is icreased stepwise from 180° to 230° C. in the course of from 2 to 3 hours, the same $H_2/N_2$ feed being maintained, and the hydrogen content of the gas entering the reactor is then increased from 1% to 100% in the course of from 4 to 5 hours.

The reactor is operated under 50 bar and at 250° C., using a metal carbonyl-containing synthesis gas (71% of $H_2$, 19% of CO and 10% of $CO_2$). After an operating time of several weeks, the activity of the catalyst, expressed as the amount of crude methanol produced, decreases to 79% of the initial value.

To regenerate the damaged catalyst, the reactor system is first flushed with nitrogen, after which an oxygen-containing regenerating gas (nitrogen containing 0.2–0.5% of $O_2$) is passed into the reactor under atmospheric pressure, this procedure being carried out continuously. The space velocity of the gas is 3,500 l (S.T.P.) per kg per hour. During the regeneration, the reactor temperature is kept constant at 150±5° C. to avoid excessively high temperatures. After 24 hours, the catalyst is reactivated by reduction, in the manner described above. After treatment with the synthesis gas described above, the activity of the catalyst, measured as the amount of crude methanol, has increased to 88% of the initial value. The rate of deactivation of the regenerated catalyst is no higher than that of the fresh catalyst. Samples removed show that the iron carbonyl and nickel carbonyl which are present as catalyst poisons in the synthesis gas result in damage, this being evident from the iron and nickel contents, which, particularly in the gas inlet zone, are higher compared with fresh catalyst.

EXAMPLE 2

The catalyst used in Example 1 is activated in the same manner by reduction, and is then treated for a relatively long time with a synthesis gas consisting of $H_2$, CO and $CO_2$ (molar composition 75:20:5) and containing traces of a catalyst poison such as nickel carbonyl, the procedure being carried out in a quasi-isothermal tube reactor under 50 bar and at 260° C. When the activity of the catalyst (determined as the amount of crude methanol) has fallen to 88% of the initial value, the catalyst is regenerated by oxidation as described in Example 1, this being done by treating it for 68 hours with an $O_2/N_2$ mixture (containing 0.2–0.5% of $O_2$) at 150° C. under atmospheric pressure. Despite the fact that about 3% of the catalyst material is removed, the amount of crude methanol produced after the subsequent reductive activation, ie. 94% of the initial value, is higher than the amount produced before regeneration. Catalyst samples which are removed show an increased nickel content at the reactor inlet.

EXAMPLE 3

An industrial low pressure methanol catalyst containing 36% by weight of CuO, 48% by weight of ZnO and 3% by weight of $Al_2O_3$ is converted to its active form by reduction in a virtually isothermally operated industrial reactor which forms the core of a complete methanol synthesis cycle, the procedure being carried out by a circulation method. The reducing agent used is hydrogen. Before the activation is started, the cycle is flushed with nitrogen and filled with it, snd a superatmospheric pressure of 4 bar is established. The recycle gas is heated at 180° C. The reductive activation is started by feeding hydrogen into the recycle gas so that the $H_2$ concentration at the reactor inlet is ≦0.5 vol. %. When the reaction has started, which is evident from a slightly increased temperature ($\Delta T < 10°$ C.) in the uppermost catalyst layer and from the presence of water of reduction instead of hydrogen in the gas emerging from the reactor, the hydrogen feed is increased so that the theoretically required amount of $H_2$ is fed in over one day, and at the same time the amount of recycle gas is chosen so that the hydrogen content of the gas entering the reactor does not exceed 1–1.5 vol. %. The course of the reduction is monitored via the catalyst bed temperatures, the $H_2$ and $H_2O$ concentrations in the gas emerging from the reactor, and the amount of water of reduction produced. If temperature peaks which are more than 10° C. above the average bed temperature occur in the migrating reduction zone, the $H_2$ feed is reduced or interrupted until the temperature once again falls below this temperature limit. The hydrogen used for the reduction is converted virtually completely to water of reduction in the reduction zone, this water appearing in place of hydrogen in the gas emerging from the reactor. Apart from water of reduction, carbon dioxide is also formed during the reductive activation; its concentration in the synthesis cycle is kept below 15 vol. % by removing recycle gas.

The first phase of the reductive activation is complete when (1) the reduction zone, which is characterized by a slightly elevated temperature, has migrated through the catalyst bed,
(2) the content of water of reduction in the gas emerging from the reactor falls and hence
(3) the hydrogen content in this gas increases.

Subsequent reduction, which serves to activate any localized catalyst components which have not been reduced, is initiated by increasing the catalyst bed temperature stepwise by 10°–20° C./hour to 220°–230° C. When the hydrogen concentration in the gas emerging from the reactor has been equilibrated with that in the gas entering the reactor, the hydrogen feed is controlled so that the hydrogen concentration in the recycle gas doubles about every 2 hours. The subsequent reduction phase is complete when the recycle gas contains 30 vol. % of $H_2$.

The introduction of fresh gas takes place at 230° C. With the introduction of metal carbonyl-free fresh gas containing 68 vol. % of $H_2$, 16 vol. % of CO, 12 vol. % of $CO_2$, 0.04 vol. % of $H_2O$ and inert gases ($CH_4$, $N_2$) as the remainder, the methanol synthesis cycle is brought to a reaction pressure of 75 bar at a rate of 15 bar/hour. When methanol formation has begun, the catalyst bed temperature is increased to 245° C. The methanol synthesis is carried out under these conditions, and with a ratio of fresh gas to gas entering the reactor of 6 kg/kg and a fresh gas space velocity of 0.5 tonnes per tonne of catalyst per hour, until the specific methanol production has decreased to 80% of the initial value. This methanol production corresponds to a catalyst activity of 26% of the initial activity if the catalyst activity is expressed as the reaction rate constant $k_o$ in a kinetic model of the form $r = k_o \cdot e^{-B/T} \cdot f(P_{H2}, P_{CO}, P_{CO2}, P_{CH3OH})$, where r is the reaction rate.

The reaction is then interrupted by letting down the synthesis cycle to a pressure of 2 bar at a rate of 15 bar/hour, and decreasing the catalyst bed temperature to 220°–230° C. Directly thereafter, the synthesis cycle is flushed repeatedly with nitrogen, this being carried out by a cycling operation, so that the nitrogen is forced into the cycle in the course of one hour until the pressure reaches 10 bar, and is then let down again to 2 bar over the same period. After the first flushing operation, the catalyst bed temperature is reduced to 170° C. Flushing with nitrogen is continued until hydrogen and CO are no longer detectable in the recycle gas (<1 vol. %).

The regeneration is started by feeding air, at 170° C., into the cycle filled with nitrogen. The pressure is 2–5 bar at the reactor inlet, and the oxygen content of the gas entering the reactor is not more than 0.5 vol. %. In the starting phase of the regeneration, the amount of air is 2–3 $m^3$ (S.T.P.) per tonne of catalyst per hour. When the regeneration has begun, which is evident from a slight increase in temperature ($\Delta T \leq 10°$ C.) in the uppermost catalyst layer, the air feed is increased to 5 $m^3$ (S.T.P.) per tonne of catalyst per hour in the course of one hour and, after a further hour, is then increased to 10 $m^3$ (S.T.P.) per tonne of catalyst per hour in the course of one hour. After the reaction has started, the oxygen content of the gas entering the reactor is kept at below 1 vol. %, while the oxygen content of the gas emerging from the reactor should not exceed 0.2 vol. % in the first few hours of the regeneration. If in either case higher values are found, the air feed is interrupted.

The course of the regeneration is monitored via the passage of the reaction zone, the temperature of which is $\leq 10°$ C. higher ($\Delta T$) than the average bed temperatures. If temperature peaks $\Delta T > 10°$ C. occur, the air feed is reduced or interrupted until the temperature once again falls below this limit. Formation of carbon dioxide is observed during the regeneration. The pressure of the reaction system is kept constant (2–5 bar) by removing recycle gas.

The main phase of the regeneration is complete when
(1) the reaction zone, which is characterized by a slightly elevated temperature, has migrated through the catalyst bed and
(2) the oxygen content of the gas emerging from the reactor is more than 80% of the oxygen content of the gas entering the reactor.

To regenerate any localized catalyst components which have not been regenerated, the air feed is then continued at 20 $m^3$ (S.T.P.) per tonne of catalyst per hour, until the oxygen concentrations in the inlet and outlet gases of the reactor have equilibrated and are not less than 10 vol. %. As a preparatory step for the reductive activation, the catalyst bed temperature is then increased to 180° C. at a rate of 10° C./hour, and at the same time the synthesis cycle is flushed with nitrogen as described above, until the oxygen content in the recycle gas has fallen to less than 0.2 vol. %. The regenerated catalyst is then activated reductively as described above, under superatmospheric pressure of 4 bar and using a cycling procedure, after which the fresh gas described above is fed into the synthesis cycle. When the process is started up once again, the activity of the regenerated catalyst is 86% of the initial value achieved using fresh catalyst, the activity being expressed as a reaction rate constant, in the above form. Under the conditions stated above, the specific methanol production is then 98% of the initial value.

We claim:

1. A process for the preparation of methanol by catalytic conversion of a synthesis gas mixture, containing hydrogen, carbon monoxide, carbon dioxide and/or water, at from 200° to 320° C. and under from 30 to 300 bar in adiabatic and/or isothermal reactions in the presence of a catalyst containing copper and zinc, wherein the fresh catalyst is first reduced with a hydrogen-containing gas before the start-up of the process, under atmospheric or slightly superatmospheric pressure at temperatures increasing from 150° to 250° C., the reduction being contained until the formation of water from the reduction reaction substantially declines, and then the synthesis is started under conventional conditions and is continued until the formation of methanol in the reaction zone has declined substantially, after which the reaction is interrupted and the catalyst is immediately flushed with an inert gas at from 10° to 300° C. and is regenerated in situ wherein the regeneration is carried out under atmospheric or moderately superatmospheric pressure, by passing an oxygen-containing gas over the catalyst at from 150° to 200° C., the oxygen content being adapted to the particular temperature during the entire course of the regeneration, and the passage of the oxygen-containing gas continuing until the peak of the temperature profile has moved across the entire catalyst.

* * * * *

UNITED STATES PATENT AND TRADEMARK OFFICE
CERTIFICATE OF CORRECTION

PATENT NO. : 4,623,668

DATED : November 18, 1986

INVENTOR(S) : Broecker et al.

It is certified that error appears in the above-identified patent and that said Letters Patent is hereby corrected as shown below:

On the title page.
Foreign Application Priority Data should read:

... Fed. Rep. of Germany...3318855 not 331855

Signed and Sealed this

Tenth Day of February, 1987

Attest:

DONALD J. QUIGG

Attesting Officer

Commissioner of Patents and Trademarks